United States Patent [19]

Lee et al.

[11] Patent Number: 4,994,165
[45] Date of Patent: Feb. 19, 1991

[54] LIQUID JUNCTION COUPLING FOR CAPILLARY ZONE ELECTROPHORESIS/ION SPRAY SPECTROMETRY

[75] Inventors: Edgar D. Lee, Olathe, Kans.; Thomas R. Covey, Ithaca, N.Y.; John D. Henion, Ithaca, N.Y.

[73] Assignee: Cornell Research Foundation, Inc., Ithaca, N.Y.

[21] Appl. No.: 311,500

[22] Filed: Feb. 16, 1989

[51] Int. Cl.$^5$ .................... G01N 27/26; B01D 57/02
[52] U.S. Cl. .............................. 204/299R; 264/180.1
[58] Field of Search ............ 204/299 R, 183.3, 180.1

[56] References Cited

U.S. PATENT DOCUMENTS

| | | | |
|---|---|---|---|
| 3,997,298 | 12/1976 | McLafferty et al. | 23/253 R |
| 4,298,795 | 11/1981 | Takeuchi et al. | 250/282 |
| 4,391,778 | 7/1983 | Andresen et al. | 422/89 |
| 4,607,163 | 8/1986 | Mizuno | 250/281 |
| 4,705,616 | 11/1987 | Andresen et al. | 204/299 R |
| 4,708,782 | 11/1987 | Andresen et al. | 204/299 R |
| 4,842,701 | 6/1989 | Smith et al. | 204/180.1 |
| 4,885,076 | 12/1989 | Smith et al. | 204/299 R |

FOREIGN PATENT DOCUMENTS 8807888 10/1988 World Int. Prop. O. .

OTHER PUBLICATIONS

Smith et al, "Improved Electrospray Ionization Interface for Capillary Zone Electrophoresis–Mass Spectrometry", *Analytical Chemistry*, 1988, 60, 1948–1952.
Udseth et al, "Capillary Isotachophoresis /Mass Spectrometry", *Analytic Chemistry*, 1989, 226–232.
Lee et al, Biomedical and Environmental Mass Spectrometry, vol. 18, 844–850 (1989).
Kennedy, R.T. et al, *Science*, 246:57–63 (1989).
Fenn, J.B. et al, *Science*, 246:64–71 (1989).
Lee, E. et al, *J. Chromatogr.*, 458:313 (1988).
Covey, T.R. et al, *Rapid Commun. Mass Spectrom.*, 2:249 (1988).

Lee, E.D. et al, *J. Microcolumn Seperations*, 1:14–18 (1989).
Brunis et al., Anal. Chem., 59:2642–2646 (1987).
Olivares, J.A. et al, Anal. Chem., 59:1230–1232 (1987).
Smith, R.D. et al., Anal. Chem., 60:436–441 (1988).
Wallingford, R.A. et al, Anal. Chem., 59:1762–1766 (1987).
Skekhar Hattangadi, Industrial Chemist, pp. 11–12, Feb. 1988.
Smith, R.D. et al, Anal. Chem., 60: 1948–1952, Sep. 15, 1988.

(List continued on next page.)

*Primary Examiner*—John F. Niebling
*Assistant Examiner*—John S. Starsiak, Jr.
*Attorney, Agent, or Firm*—Jones, Tullar & Cooper

[57] ABSTRACT

An improved capillary zone electrophoresis (CZE)/mass spectrometer interface comprises a liquid junction adapted to makeup the volume/flow rate of the CZE column eluent stream to be more compatible with the ion spray LC/MS interface flow rates required by mass spectrometer detectors in on-line separation/detection systems for variouscompositions and mixtures including biological fluids and environmental samples. Analytes eluting from the CZE capillary column are diluted with a suitable buffer thereby adjusting the volume and flow rates to prevent flow and pressure discrepanies which would otherwise result in peak broadening.

The new liquid junction system for CZE/MS and CZE/MS/MS is useful in separating, detecting and analyzing compositions and mixtures such as amino acids, pesticides, peptides, mucleotides, sulfonated azo dyes and enzymatic digests such as tryptic digest of recombinant bovine somatotropan. Detection can be carried out in both positive and negative ion modes. High separation efficiencies ranging from 50,000 to 1,000,000 theoretical plates and peak asymmetries of 1.2 to 1.8 for tryptic digest are achieved.

19 Claims, 10 Drawing Sheets

OTHER PUBLICATIONS

Minard, R.D. et al, paper ROC 945 Capillary Zone Electrophoresis/Continuous Flow FABMS–abstract of presentation 36th Annual Conference on Mass Spectrometry and Allied Topics, Jun. 5–10, 1988, San Francisco, CA.

Lee et al, "On-Line Capillary Zone Electrophoresis/Ion Spray Tandem Mass Spectrometry Determination on Small Peptides"; 36th Conference on Mass Spectrometry and Allied Topic Jun. 5–10, 1988, San Francisco, CA.

Journal of Chromatography, 458:313–321 (1988).

Covey et al, "Capillary Zone Electrophoresis/Mass Spectrometry of Sulfonated Azo Dyes"–36th ASMS Conference on Mass Spectrometry and Allied Topics, Jun. 5–10, 1988, San Francisco, CA.

Brunis et al., "Electrospray LC/MS with an Atmospheric Pressure Ionization Tandem Quadrupole Mass Spectrometer".

Udseth, Harold R. et al., Anal. Chem. 61:228–232 (1989).

LIQUID JUNCTION COUPLING FOR CAPILLARY ZONE ELECTROPHORESIS/ION SPRAY SPECTROMETRY

This invention was made in part under EPA Cooperative Agreement GR811661-01-0. The United States has certain rights to this invention.

The invention relates to an improved liquid junction interface interposed between a zone electrophoresis system for separating compositions and mixtures and a mass spectrometer (MS) detector. In a preferred mode the invention relates to an interface between the CZE column and an ion spray unit operated at atmospheric pressure which in turn is positioned in series with the mass spectrometer.

BACKGROUND OF THE INVENTION

Electrophoresis is a powerful technique for the separation of charged species in solution. Capillary zone electrophoresis (CZE) was first introduced by F. E. P. Mikkers and coworkers and later explored by J. W. Jorgenson and coworkers. Jorgenson developed electrophoresis processes with on-column detection. Research continues for new apparatus and methods for analyte characterization using electrophoresis and on-line detection. Heretofore most detectors have been optical detectors based on UV absorbance and fluorescence emission. Mass spectrometry is particularly suited for detection of CZE eluents with high sensitivity and selectivity.

Ion evaporation offers a preferred ionization mechanism for on-line CZE/MS because separated components already exist as charged species in the CZE buffer. Ion evaporation involves the emission of ions from the condensed phase into the gas phase and is a mild form of ionization for polar and ionic compounds. This process is one of the main mechanisms of ionization occurring in thermospray, fast atom bombardment, and electrospray ionization. Thermospray does not appear feasible for CZE/MS coupling due to the high liquid flowrates presently required for thermospray ionization and the apparent sensitivity limitations in comparison to other mass spectrometric techniques. Preliminary results demonstrating feasibility of coupling CZE and MS using a continuous atom bombardment (FAB) interface have been presented by R. D. Minard and coworkers (Paper ROC 945, 36th Annual Conference on Mass Spectrometry and Allied Topics June 5-10, 1988); however, excessive bandbroadening and loss of separation efficiency occurred due to the long transfer line to the FAB ion source and the associated high vacuum requirements. Wallingford and Ewing (*Anal. Chem.*, 59:1762-1766, 1988) previously reported an interface for electrochemical detection based on a porous glass joint created in the column near the cathodic end of the CZE. The porous glass joint along with the cathode end of the capillary were submersed in a buffer reservoir for the purpose of permiting "the application of a potential gradient over one segment of capillary".

The electrospray ionization liquid interface for mass spectrometry developed by Fenn and coworkers has been used by R. D. Smith and coworkers to demonstrate the feasibility of CZE coupled to a mass spectrometer (*Anal. Chem.*, 60:436-441 (1988)). In the Smith system the last few cm of the cathode end of the CZE capillary was sheathed with a stainless steel capillary and silver was vapor-deposited at the end of the two capillaries to make good electrical contact with the buffer flowing from the inside of the CZE capillary. The cathode end was used as the electrospray electrode for electrospray ionization. Although feasibility was demonstrated, this interface required high CZE electroosmotic flows and low buffer concentrations to maintain stable electrospray conditions.

Although the prior art systems have suggested the combination of CZE for separating multiple component analytes with mass spectrometer detection, such systems using an ion spray interface operated at atmospheric pressure suffer from band broadening of the separated species due to the discrepancy of flow rates between the zone electrophoresis separator (0.1 to 1.0 $\mu$L/min flow) and the flow rates (1.0 to 50 $\mu$L/min) required by the ion spray interface to accommodate the entire CZE eluent. The present invention relates to a fluid coupling of CZE and the ion spray LC/MS interface that allows for a wide range of electroosmotic flows without compromise of the CZE separation.

A BRIEF SUMMARY OF THE INVENTION

The present invention relates to an apparatus for separating and detecting small amounts of components of an analyte stream comprising an electrophoresis separator, an ion spray mass spectrometer (MS) system and a means for adding a fluid to the analyte stream between the electrophoresis separator and the ion spray mass spectrometer in an amount which increases the flow rate of the analyte stream exiting the electrophoresis separator and makes it compatible with the flow rate required by the ion spray interface and MS detector to allow detection of the separated components at high sensitivity and without substantial peak broadening.

Another object of the invention relates to the above-described apparatus wherein the fluid comprises a buffer or a buffer plus an inert gas nebulizer, the analyte stream eluent in the electrophoresis separator has a flow rate of from about 0.1 $\mu$L/min to about 1.0 $\mu$L/min and the flow rate of the eluant, after addition of make-up buffer, entering the ion spray mass spectrometer has a flow rate of from about 1.0 $\mu$L/min to about 50 $\mu$L/min; wherein said electrophoresis separator is selected from the group consisting of moving boundary electrophoresis, isotachophoresis, zone electrophoresis and isoelectric focusing separators.

A further object of the invention is a liquid junction interface, for coupling a zone electrophoresis separation column with an ion spray mass spectrometer wherein said junction comprises a means for adjusting the flow rate of the zone electrophoresis column eluent passing to a mass spectrometer detector in an amount which makes said flow rate compatible with the ion spray interface and said spectrometer in on-line separation/detection of analyte compositions and mixtures, wherein said adjusting comprises the addition of buffer to said eluent, said interface comprising a zone communicating with:

(1) the exit end of the electrophoresis column;

(2) a conduit having a first end proximate to (1) but separated therefrom to form a gap and a second end communicating with the ion spray mass spectrometer;

(3) a reservoir adapted to contain and supply make-up buffer to said zone and to surround (1) and the first end of conduit (2) including the said gap separating (1) and said first end of conduit (2); said liquid junction interface further comprising a means for adjusting said gap;

wherein said electrophoresis column is preferably a silica capillary column and said conduit is preferably a stainless steel capillary column.

Yet another object of the invention relates to a process for analyzing at high separation efficiency small amounts of biological components which combines an electrophoresis separation with an on-line detection of charged particles using an ion spray mass spectrometer system operated at atmospheric pressure which comprises:

(1) passing a biological sample analyte through a CZE capillary separation column to separate the sample components;

(2) adding make-up buffer to the eluent exiting the CZE column in an amount which increases the flow rate of the eluent to make it compatible for detection in an ion spray mass detector system;

(3) conducting the eluent with added buffer to an ion spray mass spectrometer system and detecting said sample components at high separation efficiency without substantial peak broadening.

DETAILED DESCRIPTION OF THE INVENTION

The present invention relates to an apparatus and method for the analysis of extremely small amounts of compounds or mixtures including extracts biological fluids based on separation by capillary zone electrophoresis (CZE) and detection by on-line by mass spectrometry wherein the flow rate of the eluent exiting the CZE is increased by addition of make-up fluid comprising buffer.

More specifically the invention relates in a preferred mode to a novel liquid junction for joining a capillary zone electrophoresis (CZE) capillary column, usually a fused silica capillary column with a second capillary conduct, usually stainless steel capillary communicating with an ion spray LC/MS interface using an atmospheric pressure ionization triple quadruple mass spectrometer. The said liquid junction comprises a means for increasing the flow rate by adding makeup buffer to the analyte eluent exiting the CZE separation column prior to entering the ion spray MS detector.

The purpose of the liquid junction interface for coupling an electrophoresis separator with a mass spectrometer detector is to allow the analyte stream exiting the separation column to be combined with additional fluid, preferably a buffer, to make the analyte stream flow rates suitable for detection via the ion spray mass spectrometer system which if not adjusted would result in peak broadening, current instability and decreased sensitivity. As shown in FIG. 2, the capillary tubing leading to the ion spray interfaced with the mass spectrometer is often surrounded with a concentric tubing, such as a stainless steel tubing, for the purpose of conducting an inert gas (nitrogen) stream to nebulize the liquid exiting the electrophoresis separator and ion spray interface. In such instances, make-up buffer added at the liquid junction compensates for the aspiration effect of nitrogen flow in the concurrent tubing communicating with the analyte stream. The net result is that the gas nebulizes the analyte constituents and the added buffer adjusts the flow rate of the analyte stream passing to the ion spray mass spectrometer system for detection purposes. Various modes of addition of buffer to the analyte stream will be apparent to one skilled in the art. Make-up buffer may be added via the liquid junction interface shown in FIG. 1. Alternatively, buffer may be added to the nebulizing gas stream.

Figure 1A:
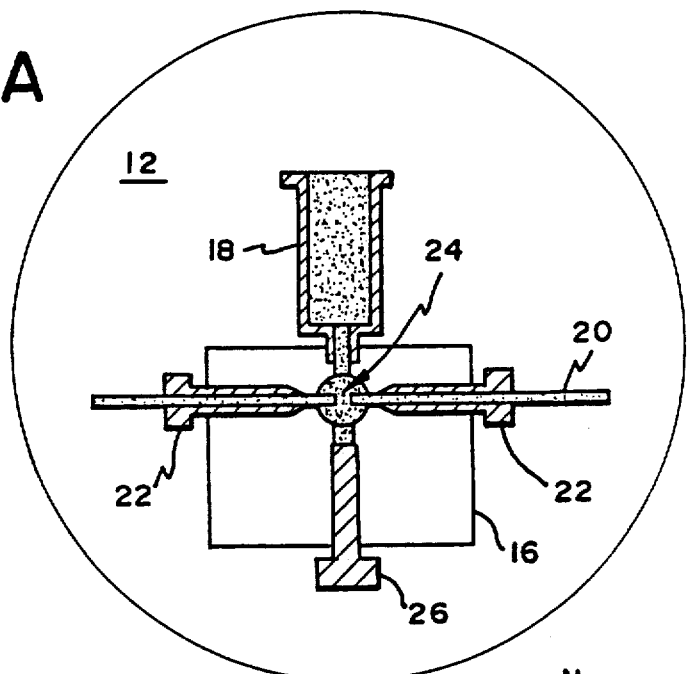
FIG. 1 is a schematic drawing of a liquid junction coupled CZE/ion spray mass spectrometry system having (2) 0–60 kV high voltage power supply, (4) dual-purpose carbon buffer reservoir and high voltage electrode, (6) capillary separation column, (8) ion spray interface, (12) liquid junction coupling, (16) modified stainless steel tee, (18) polyethylene syringe barrel, (20) stainless steel capillary ion spray electrode, (22) reusable capillary fittings, (24) liquid junction gap, (26) removable plug, (30) stainless steel tee, (32) nebulization gas inlet, (34) concentric tube for nebulizing liquid effluent, (36) ion spray voltage power supply, (38) mass spectrometer interface plate, (40) mass spectrometer ion extraction orifice, (44) mass analyzer; also seen in FIG. 1 is an exploded view of one type of liquid junction coupling (12).
Figure 1:
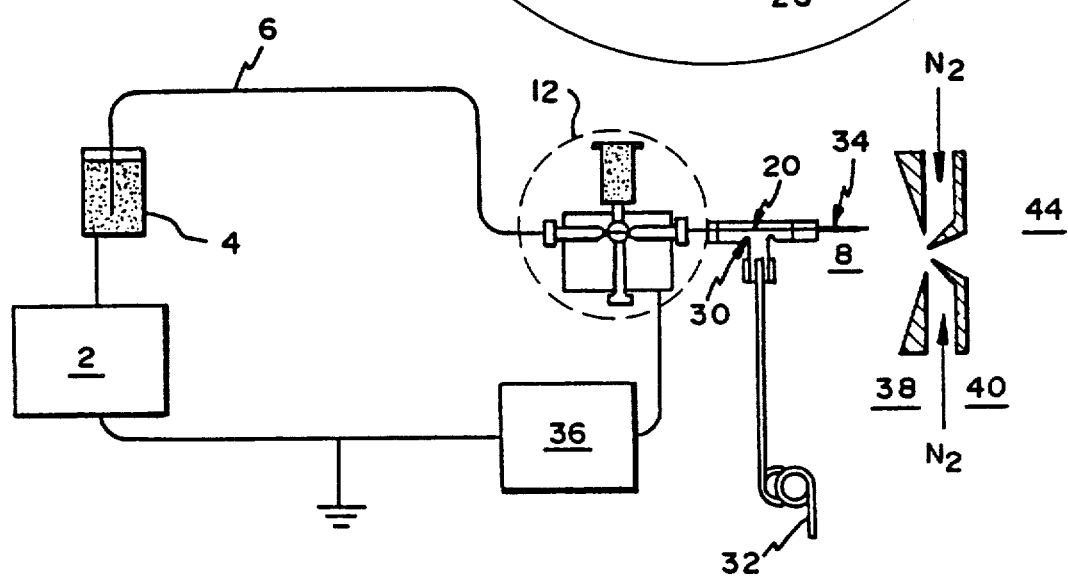
Figure 2:
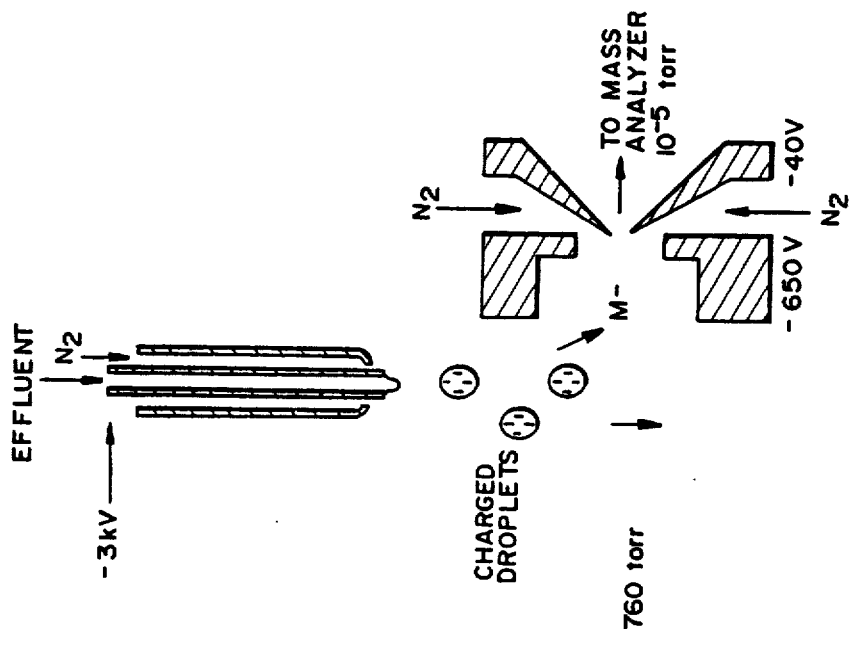
FIG. 2 schematically illustrates an atmospheric pressure ion spray interface for the mass spectrometer wherein the electrophoresis separated eluent is nebulized with nitrogen to give charged droplets and gas phase ions which may be focused to the mass analyzer.

A schematic illustration of the instrumentation is shown in FIG. 1. The capillary electrophoresis system consisted of 0–60 kV voltage regulated power supply (2) (Spellman, Model RHR60P30/EI, Plainview, N.Y.). The high voltage lead was connected directly to a 2-mL volume carbon vessel (4) which served the dual purpose of buffer reservoir and electrode. The separation column (6), a 100-um i.d. × 100-cm length of fused-silica capillary (Polymicro Technologies, Phoenix, Ariz.), was suction-filled with buffer and the anode end of the column suspended in the carbon vessel (4) containing the buffer medium. The cathode end of the column was connected to the ion spray LC/MS interface (8), as described by A. P. Bruins et al, *Anal. Chem.*, 59:2642–2646 (1987), via a liquid junction coupling (12). Sample volumes of 2 to 30 nL were introduced onto the column at the anode end by hydrostatic or electrokinetic injection (as described by X. Huang et al, *Anal. Chem.*, 60:375–377 (1988). The sample volume was determined by injecting a narrow band of a dark dye and measuring the time for it to pass through a given length of the column while in the inject mode. The capillary electrophoretic separation commenced by applying 30 kV to the anode end of the separation column through the carbon buffer reservoir while + or −3 kV was applied to the cathode end via the ion spray LC/MS interface (8) and the liquid junction coupling (12). This produced a net CZE voltage of 27 kV for positive ion operation and 33 kV for negative ion operation of the mass spectrometer.

The liquid junction coupling shown expanded in schematic FIG. 1 was constructed from a standard 1/16-in. stainless steel tee (16) (Waters, Milford, Mass.). The tee was drilled with a 5/64-in. drill through the top and fitted with a 3-mL volume polyethylene syringe barrel (18) (Monoject, St. Louis, Mo.). The cathode end of the column (6) and the end of the electrospray electrode (20) from the ion spray LC/MS interface were positioned in the center of the tee opposite each other with reusable capillary fittings (22) (Upchurch, Oak Harbor, Wash.). The gap (24) between the end of the column and the end of the electrode was adjusted to 25 um under a microscope. This gap could be easily adjusted by tightening or loosening the capillary fittings (22). The hole opposite the syringe barrel in the tee was fitted with a removable plug (26). The plug was removed for alignment and adjustment of the gap between the column and electrode and when initially filling the syringe barrel and tee with buffer to eliminate air trapped in the tee.

FIG. 2 shows the ion spray LC/MS interface used which was based on the design reported previously by Bruins, Covey and Henion, *Anal. Chem.*, 59:2642–2646 (1987). The central electrospray electrode (20) through which the eluent flowed was a 100-um i.d. ×200-um o.d. stainless steel capillary (Small Parts, Gainsville, Fla.). The electrode passed through a 1/16-in. stainless steel tee (30) (SGE, Austin, Tex.). Nitrogen gas for assisting the electrospray nebulization was introduced through the side port (32) of the SGE tee and exited at the end of the electrospray electrode at a velocity of approximately 300 m/s through a concentric 325-um i.d. stainless steel tube (34). The end of the electrode protruded 500 um past the end of the concentric tube. A 0–10 kV voltage and current regulated power supply (36) (Spellman, Model RHR10PN30/FG, Plainview, N.Y.) was used to float the ion spray LC/MS interface (8) and the liquid junction coupling (12) at an electrospray potential of +3 kV or −3 kV for positive or negative ion operation, respectively. The interface plate (36) of the mass spectrometer served as the counter electrode for the ion spray interface. The end of the ion spray electrode was positioned 1.5 cm away from the skimmer cone (40) of the mass spectrometer and 0.5 cm off-axis.

A SCIEX TAGA 6000E triple quadruple mass spectrometer (Thornhill, Ontario, Canada) equipped with an atmospheric pressure ion source was used to sample ions produced from the ion spray LC/MS interface (8). Ions were sampled into the vacuum for mass analysis through a 100-um i.d. orifice in the end of a skimmer cone (40) which was extended towards atmosphere. The atmospheric side of the cone (40) was purged with a curtain of high purity, dry nitrogen gas. The nitrogen curtain acted as a barrier to restrict contaminants and solvent vapor from entering the mass spectrometer vacuum. High vacuum in the analyzer region (44) of the mass spectrometer was achieved by cryogenically-cooled surfaces maintained at 15–20 K surrounding the quadruple mass filter. During routine operation the indicated high vacuum was $7 \times 10^{-6}$ torr and during collision-induced dissociation (CID) the vacuum was $1.5 \times 10^{-5}$ torr with a target gas thickness of $230 \times 10^{12}$ atoms/cm$^2$ of ultra-pure argon or $150 \times 10^{12}$ atoms/cm$^2$ of ultra-pure xenon (Matheson, Secaucus, N.J.) in the collision cell. A collision energy of 50 V energy was used for all CID experiments.

Previous LC/MS experience with electrospray demonstrated that the assistance of pneumatic nebulization improves the stability of electrospray. Therefore, the ion spray LC/MS interface was directly coupled to the end of the CZE column with a low-dead volume union between the capillary electrode and the column exit. The ion spray LC/MS interface gave improved stability, but still required high electroosmotic flows through the column. If low electroosmotic flows were used the siphoning action of the field generated from the electrospray potential in combination with the aspirating effect of the nebulizing gas pulled on the buffer in the capillary. The increased flow through the capillary resulted in shorter retention times and degraded separation when compared to work with on-column UV detection. The decrease in the buffer volume was measured for a given period of time from an unrestricted reservoir coupled directly to the ion spray LC/MS interface. The combination of the potential field and the aspiration of the nebulizing gas can siphon at flow rates as high as 50 uL/min. However, typical flow rates were in the range of 10 to 20 uL/min. When fused-silica columns are used CZE generally operates at flow rates of less than 2 uL/min from the electroosmotic flow in the column or even well below 1 uL/min with buffers that have low pH and high ionic strength. On the other hand, generation of stable electrospray conditions are difficult at flow rates below 1 uL/min.

Figure 3:
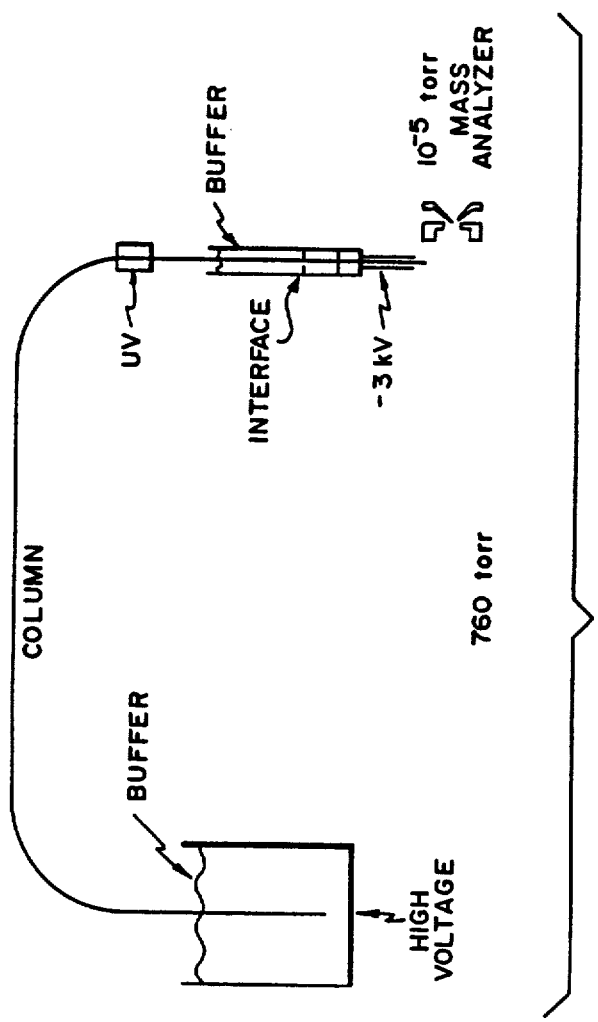
FIG. 3 is a schematic of the Capillary Zone Electrophoresis/Mass Spectrometer showing an interface system for adding buffer to the CZE column eluent using atmospheric pressure ion spray ionization.

Due to the incompatibility of the flowrates of CZE and ion spray a liquid junction for coupling CZE and ion spray mass spectrometry was developed. The liquid junction exemplified in FIGS. 1 and 3 allow the addition of buffer from a reservoir source over a wide range of flows (0 to 20 uL/min). The possibility of using zero flow provides the opportunity for other forms of high performance capillary electrophoresis such as isotachophoresis and the use of gel-filled capillaries which have no liquid flow. Flows of 10 to 20 μL/min are needed for MS and atmospheric pressure/MS detectors.

In one mode the coupling (12) was constructed from a stainless steel tee (16). The cathode end of the CZE column (6) is placed opposite the end of the capillary electrode (20) of the ion spray LC/MS interface with a 25-um gap (24) between. The gap allows buffer to flow unrestricted into the ion spray interface electrode (20) from the surrounding reservoir preventing suction to occur at the end of the CZE column. The size of the gap was determined from the formula $d = R/2$ which was derived from a relation between the cross sectional area of the ion spray capillary electrode equal to the surface area around the gap, where d is the gap and R is the internal radius of the capillary electrode (20). Since the flow rate into the ion spray interface is 10 to 20 times greater than from the CZE column, analytes are rapidly swept into the mass spectrometer via the make-up buffer (in 18) to the ion spray LC/MS interface with no observable band broadening or loss of resolution.

It is recognized the gap distance will vary depending on the capillary diameter. A preferred gap opening for CZE capillary diameter of 100$\mu$ is 20 to 25 $\mu$m. When the gap is too small, not enough make-up flow enters the eluent stream; allignment problems occur and the eluting components everlap due to the increased stability of the stream entering the ion spray system. When the gap is too large, separation efficiency degrades, chromatographic (component) peaks broaden and extreme tailing destroys sensitivity.

Liquid junction coupling of CZE and the ion spray LC/MS interface does not adversely affect peak broadening and provides good reproducability. One skilled in the art will recognize that the present invention contemplates various modes for adjusting flow rates to the to the ion spray/MS interface by adding make up buffer from a buffer reservoir. Accordingly, the invention should not be limited by the best mode examples or by any specific CZE/mass spectrometer system. For example, it is contemplated that the buffer can be added to the nebulation gas stream set forth in co-pending patent application Ser. No. 202,768 filed June 3, 1988, for use with the ion spray/MS interface. For this purpose, Ser. No. 202,768 is incorporated herein by reference. The liquid junction coupling can also be used with other high performance capillary electrophoresis techniques which have zero flow such as isotachophoresis and gel filled capillaries. Other methods of increasing flow rates by adding make-up buffer downstream of the electrophoresis separation will be recognized by one skilled in the art.

Full-scan capillary zone electrophoresis/mass spectrometry (CZE/MS) and capillary zone electrophoresis/tandem mass spectrometry (CZE/MS/MS) were used for the detection of monosulfonated and polysulfonated azo dyes at the low pmole levels. Under selected ion monitoring (SIM) conditions fmole levels of the dyes were detected. Ion evaporation via the ion spray liquid chromatography/mass spectrometry (LC/MS) interface (a mild form of ionization) exhibited only deprotonated singly charged or poly-deprotonated multiply charged negative molecular ions for sulfonated azo dyes. CZE/MS/MS daughter ion scanning after collision-induced dissociation (CID) of the molecular species for all sulfonated azo dyes contained the sulfonate ion (m/z 80). The presence of three sulfonated azo dyes in a waste water extract was shown by parent ion scanning for the sulfonate daughter ion (m/z 80).

The term electrophoresis as used herein includes moving boundary electrophoresis, isotachophoresis, zone electrophoresis and isoelectric focusing.

For purposes of this invention, a preferred make-up fluid is a buffer or mixture of buffer with a nebulizing gas. The makeup buffer can be the same or different from the buffer used in the electrophoresis column. As a practical matter, it is preferred to use the same make-up buffer as used in the separation. Useful buffers include ammonium acetate, formic acid, trifluoroacetic acid, ammonium formate and the like. Useful solvents for buffer preparation include water, acetonitrile, lower alcohols including methanol and ethanol. The buffers operate over a wide variety of pH. Preferred pH is from about pH 4.2 to pH 11.

The flow rate in the CZE column and in the ion spray conduit, when used, is dependent on the diameter of the capillary or conduit. Typical flows in the CZE capillary having a diameter of 100$\mu$ is about 1.0 $\mu$L/minute. Useful flow rates in the ion spray interface are about 10 to 20 $\mu$L/minute. The purpose of the make-up buffer is to increase the flow rate of about 1.0 $\mu$L/minute up to 50 $\mu$L/minute for the satisfactory operation of the ion spray/mass spectrometer system without detriment to detection sensitivity of the analyte components separated in the CZE column.

Ion spray interface has several advantages compared to both traditional techniques (FAB, Thermospray, etc.) and electrospray. The use of pneumatic nebulization in Ion Spray results in a stable ion current from a comparatively large range of flow rates (100 nl/min to 200 $\mu$l/min). This allows the direct analysis of samples by the direct introduction of small quantities of material, as reported here, but also permits on-line connection to separation and electrophoretic techniques, such as HPLC and Capillary Zone Electrophoresis (CZE). Furthermore, the extreme sensitivity of Ion Spray (picomole levels compared to nanomole levels for similar compounds by FAB, and Thermospray, results in very low sample consumption.

Like the electrospray interface, the Ion Spray interface produces ions via ion evaporation. However, pneumatic nebulization, in addition to electric fields, is used to disperse the droplets to the sub-micron dimensions required for ion evaporation. Thus, ion spray and electrospray are distinguished by the use of pneumatic nebulization, which adds stability to the ion current and allows the use of flow rates from 100 nL/min to 200 $\mu$L/min, whereas pure electrospray operates best in the 1-20 $\mu$L/min range.

As shown by the best mode examples, the above described apparatus and process incorporating make-up buffer down stream of the zone electrophoresis separator is advantageous for the separation and detection of various complex samples including for example biological extracts, enzymatic digests, tryptic digests, ions in solution including dyes such as sulfonated azo dyes, amino acid sequences, peptide dynorphins, leucine enkephalin and the like. The examples are meant to generally exemplify the invention and should not be interpreted as limiting the scope of the invention.

EXAMPLE 1

Using the apparatus described in FIG. 1, experiments were run to determine optimum spacing of the capillary gap in the liquid junction.

Figure 4:
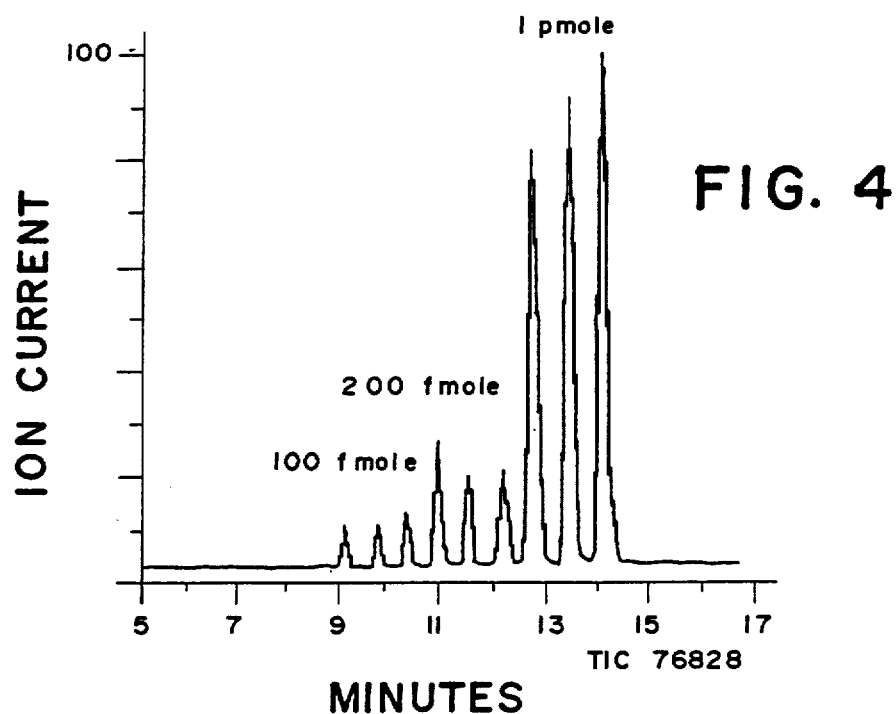
FIG. 4 is a SIM CZE/MS total ion current electropherogram from repetitive triplicate injections of 100 fmole, 200 fmole, and 1 pmole amounts of arg-vasopressin wherein the $(M+H)^{30}$ and $(M+2H)^{2+}$ ions were monitored; CZE buffer was 50/50 acetonitrile/20 mM $NH_4OAc$ and hydrostatic injections were made at a height of 5 cm for 10 seconds.

Serial injections can be made at close intervals because the flow of the CZE system can be stopped during operation by simply turning off the high voltage. Optimum spacing of the gap was confirmed experimentally by triplicate serial injections of arg-vasopressin (FIG. 4) at three different dilutions in the buffer. This experiment was accomplished in a 50/50 acetonitrile/20 mM acetate buffer at pH 6.8 wherein volumes of 20 nL were hydrostatically injected every 30 sec. The $(M+H)^{30}$ and $(M+2H)^{2+}$ ions of arg-vasopressin were monitored by the mass spectrometer under selected ion monitoring (SIM) conditions. The asymmetry measured at ten percent peak height for these peaks ranged from 1.0 to 1.3 demonstrating that the liquid junction gap is not contributing to excessive peak tailing. If wider gaps are used peak tailing is observed due to the increased residence time and mixing at the junction which resulted in asymmetric peaks. Hydrostatic injections were made at 30-sec intervals and the peaks appeared at approximately 30-sec intervals. If the gap is too narrow the peaks in a series of injections elute at increased intervals due to the suction of the ion spray LC/MS interface during the injection period in between the CZE high voltage was not operational.

Sensitivity. The sensitivity of ion evaporation via the ion spray LC/MS interface is sample dependent with the best sensitivity for samples which are already ionized in solution. For arg-vasopressin (FIG. 4) the 100-fmole injections have a signal-to-noise ratio of 19:1, suggesting detection limits in the low fmole range. High percentages of organic modifier such as acetonitrile or methanol at a low concentration (approx. 1 mM) of a buffer salt such as ammonium acetate in the CZE buffer increases the sensitivity for most analytes.

EXAMPLE 2

Determination of Pesticides and Herbicides

Figure 5:
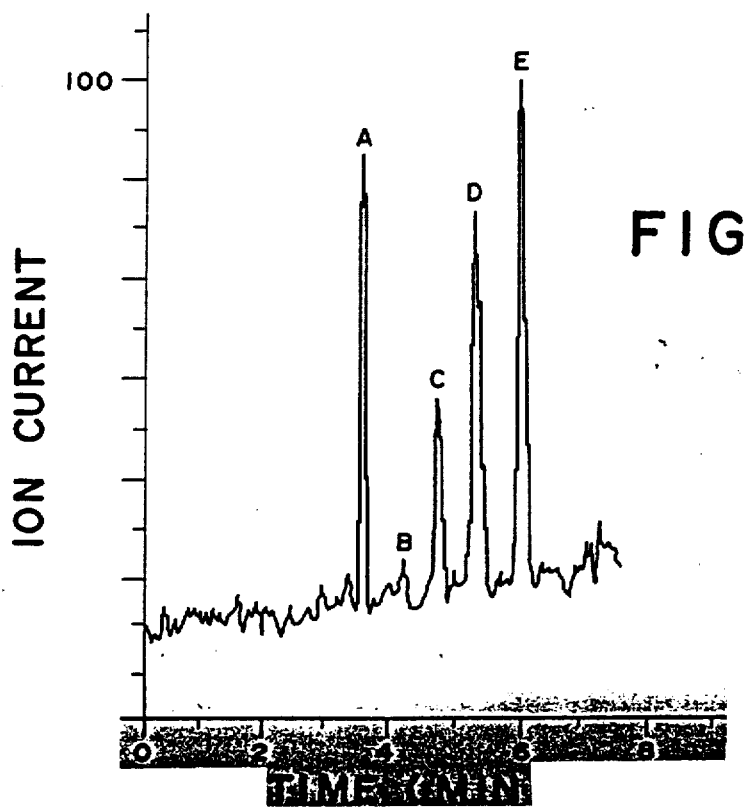
FIG. 5 shows a SIM CZE/MS ion current electropherogram for 1.2 pmole of five acid pesticides, namely 4-[2,4-dichlorophenoxyl] butyric acid (A); gibberellic acid (B); 2,3,6-trichlorophenyl-acetic acid (C); 2,4-dichlorophenoxy acetic acid (D); and p-chloromandelic acid (E).

Various pesticides and herbicides were analyzed using the apparatus described in FIG. 1. Many separations can be improved by the addition of organic modifiers and as mentioned above the sensitivity of ion spray LC/MS is also better. The CZE/MS electropherogram (FIG. 5) for 1.2 pmole per component of the acid pesticides 4-[2,4-dichlorophenoxyl] butyric acid (A), gibberellic acid (B), 2,3,6-trichlorophenyl-acetic acid (C), 2,4-dichlorophenoxyacetic acid (D), and p-chloromandelic acid (E) was produced in a 90/10 acetonitrile/0.1 M NH4OAc buffer. Under higher aqueous conditions the individual components of the mixture were not completely resolved and the retention times were longer. This presumably could be a result of acid hydrates being formed in high aqueous buffers. At high organic buffer concentration the hydration will be suppressed and different electrophoretic mobilities will be apparent depending on the binding force of the species.

EXAMPLE 3

Determination of Sulfonated Azo Dyes

The apparatus of FIG. 1 was used for the determination of disulfonated azo dye, acid blue 113. Low detection limits have previously been demonstrated by ion spray LC/MS for sulfonated azo dyes. These compounds exhibit mass spectra which contain the $(M-nH)^{n-}$ ions (n=the number of sulfate groups). Collision-induced dissociation of the $(M-nH)^{n-}$ ion produces a common daughter ion at m/z 80 for the sulfonate functionality (FIG. 6B). The CZE/MS/MS total ion electropherogram (FIG. 6A) and daughter ion mass spectrum (FIG. 6B) for the disulfonated azo dye, acid blue 113, was obtained by focusing it's $(M-2H)^{2-}$ ion at m/z 317 in the first quadruple, performing CID in the second quadruple and scanning the third quadruple from m/z 50 to 350. As expected, the sulfonate ion at m/z 80 was present as well as fragments at m/z 156 and m/z 297 in the daughter ion presumably originate from the cleavage at the azo functionalities with charge retention on the sulfonate-containing group (FIG. 6B).

The main advantage of CZE/MS over LC/MS is that there is more flexibility in the choice of buffer used. This allows the separation buffer to be tailored more to meet the needs of the mass spectrometer.

EXAMPLE 4

Figure 7:
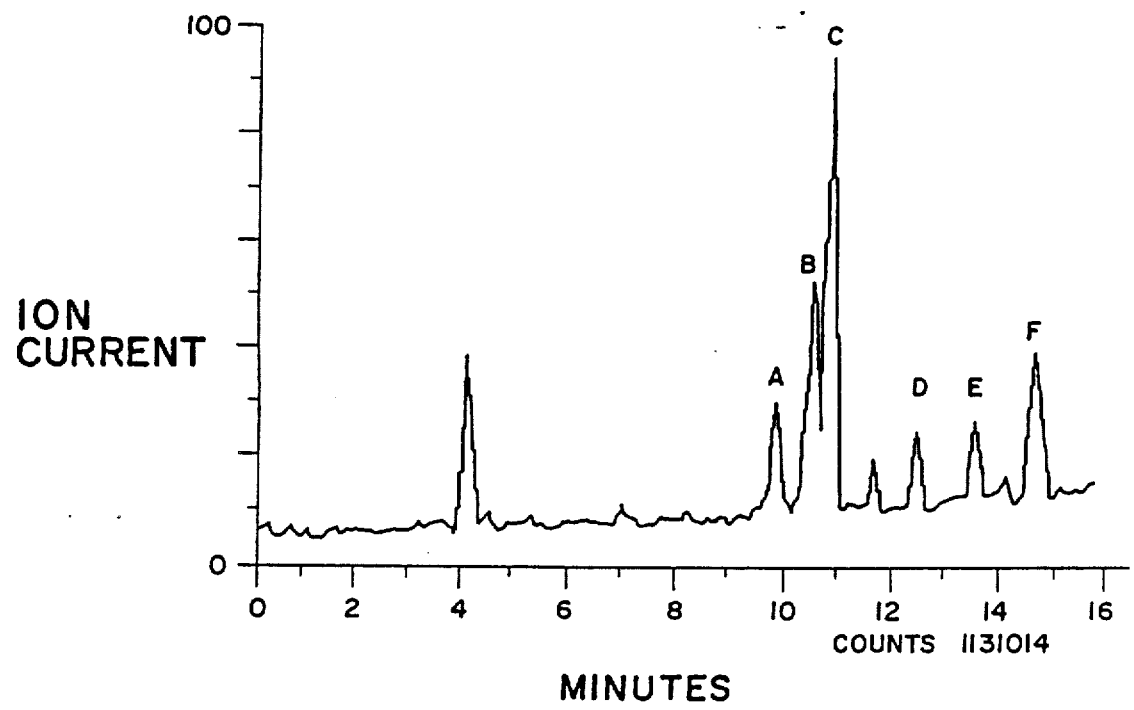
FIG. 7 is a CZE/MS/MS extracted ion electropherogram for the parent ion scan from a mixture of six sulfonated azo dyes, namely (A) acid red 151; (B) acid red 88; (C) acid orange 7; (D) acid blue 113; (E) acid black 1; and (F) acid red 14 where the ions are formed by ion evaporation at atmospheric pressure via the ion spray/MS interface.
Figure 7A:
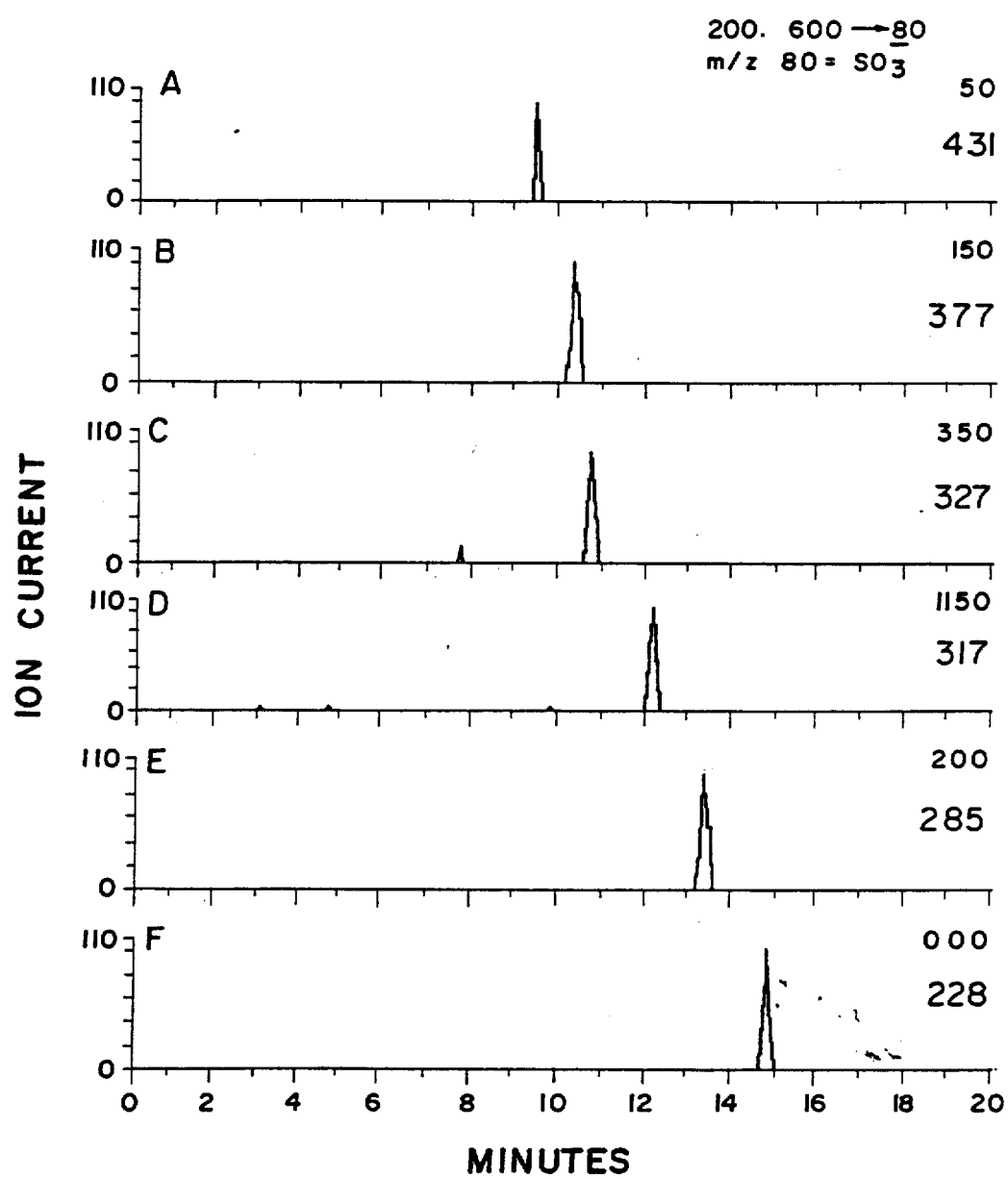
FIG. 7A is a plot of ion current versus time (minutes) for the individual sulfonated azo dye of the mixture shown in FIG. 7.

The process of Example 3 was repeated in a sulfonated azo dye mixture. Since the sulfonate ion is a common CID fragment ion of sulfonated azo dyes, parent ion scanning can be used to screen for sulfonated azo dyes. The extracted ion electropherograms (FIG. 7) for a mixture of six sulfonated azo dyes were obtained while scanning the first quadruple from m/z 200 to 600 and monitoring m/z 80 in the third quadruple. The first three components separated are the monosulfonated dyes acid red 1 (A, m/z 431), acid red 88 (B, m/z 377), and acid orange 7 (C, m/z 327) and the second three are the disulfonated dyes acid blue 113 (D, m/z 317), acid black 1 (E, m/z 285), and acid red 14 (F, m/z 228). The sulfonated azo dyes elute in decreasing m/z ratio. This observation can be explained by noting that the electrophoretic mobility of negatively charged species is toward the anode. However, the higher velocity of the electroosmotic flow, due to the negatively charge fused-silica capillary wall, causes all species to have a net migration towards the cathode. As the size of a negatively charged species increases its electrophoretic mobility decreases causing those ions of larger size and lower charge to elute first.

EXAMPLE 5

Tryptic Digest of recombinant bovine somatotropin.

Figure 6:
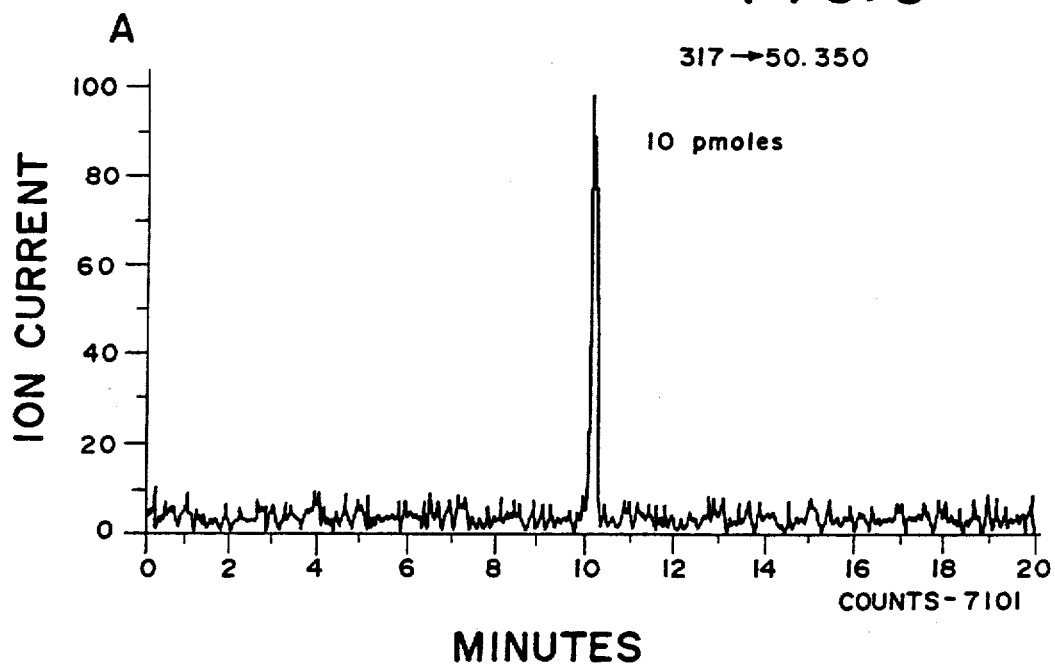
FIG. 6 shows a CZE/MS/MS total ion current electropherogram (A) and daughter ion mass spectrum (B) for the disulfonated akzo dye, acid blue 113.
Figure 6:
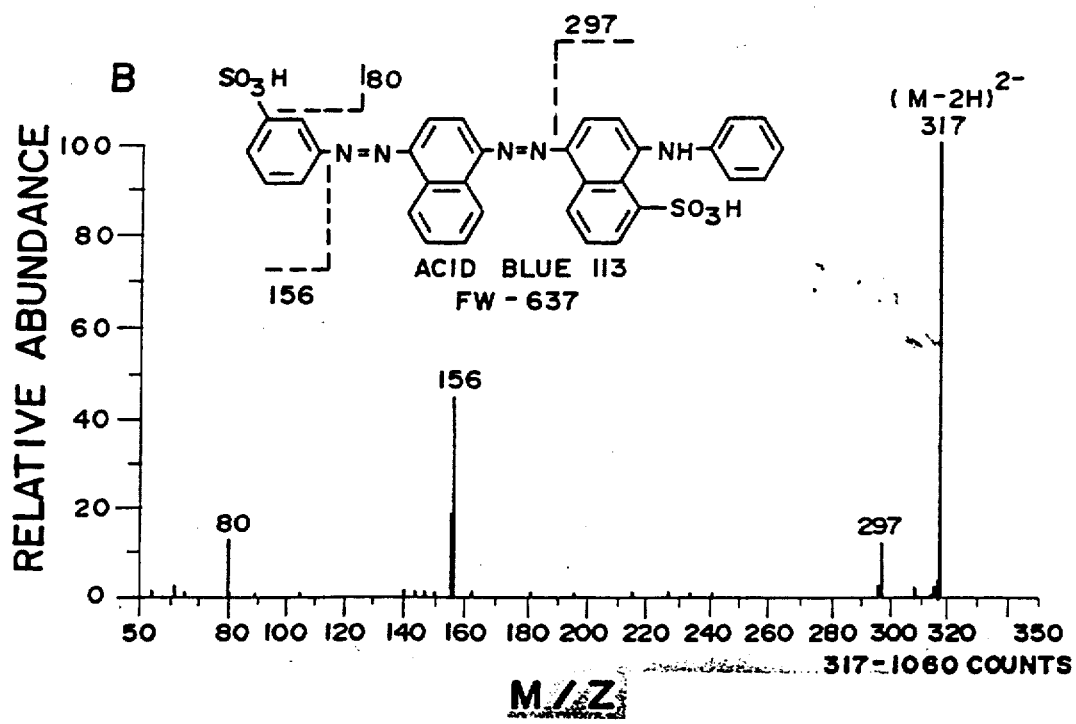

The apparatus and process of Example 3 was used to analyze tryptic digest of recombinant bovine somatotropin. The sample was supplied by Dr. F. Cron of the UpJohn Company. One characteristic of CZE is its ability to obtain high separation efficiencies. The SIM CZE/MS electropherogram (FIG. 8) for 11 components in a tryptic digest of recombinant bovine somatotropin exhibits separation efficiencies from 50,000 theoretical plates for peak A to 300,000 theoretical plates for peak K with asymmetry factors of 1.2 and 1.8, respectively. Theoretical plates were calculated from the formula $N = 5.54(tr/tw_\frac{1}{2})^2$. It would be unlikely to obtain such high efficiencies if the liquid junction coupling between the CZE capillary and the ion spray LC/MS interface were contributing significantly to band broadening. Even with the high separation efficiencies obtainable by CZE components D and E, and H and I could not be resolved from each other in the work. The mass spectrometer can be used to determine the peak purity by resolving the individual components by their mass-to-charge ration. The extracted ion electropherograms (FIG. 9) for the separation shown in FIG. 6 illustrates this point. Components D and E (peak D,E in FIG. 9) are resolved by their masses at m/z 538 and m/z 721 (FIGS. 7D,E). The same is true for components H and I (peak H,I in FIG. 9, FIGS. 7H,I).

EXAMPLE 6

Determining Peptide Sequence by CZE/MS/MS.

Figure 8:
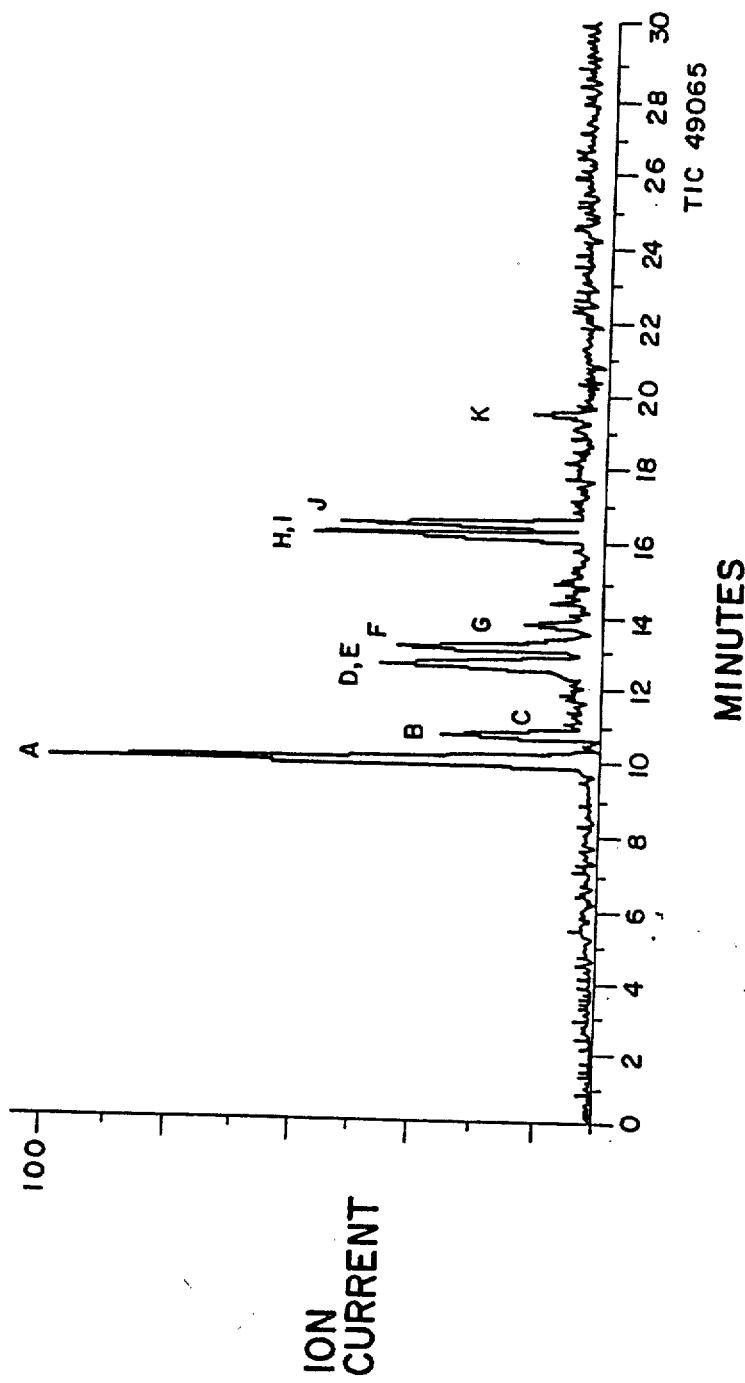
FIG. 8 shows a SIM CZE/MS total ion electropherogram for eleven components of tryptic digest of recombinant bovine somatotropin showing separation efficiencies from 50,000 theoretical plates (A) to 300,000 theoretical plates for peak K with asymmetry factors of 1.2 and 1.8 respectively.
Figure 9:
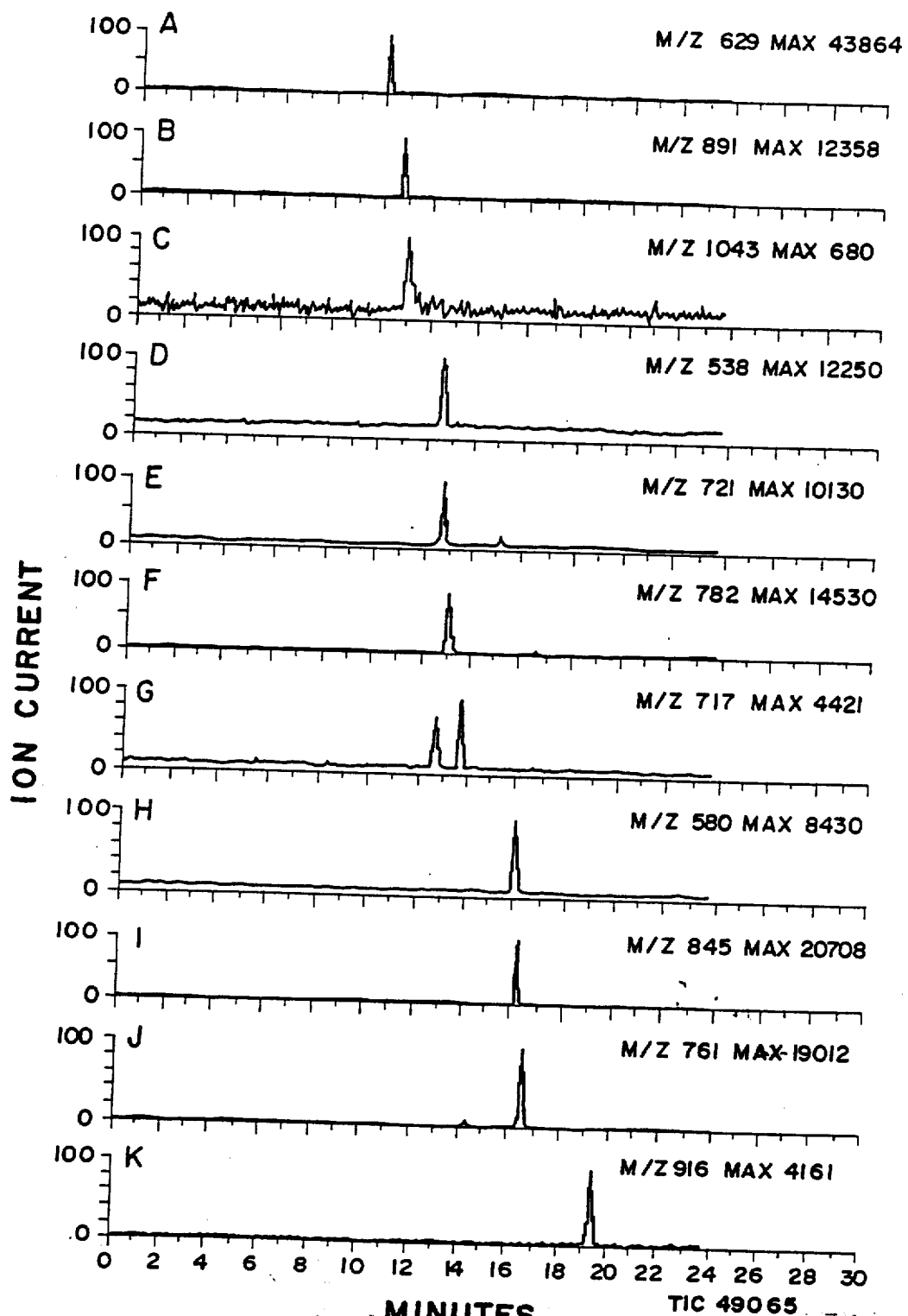
FIG. 9 shows a SIM CZE/MS extracted ion electropherogram for the tryptic digest sample of FIG. 8.
Figure 10:
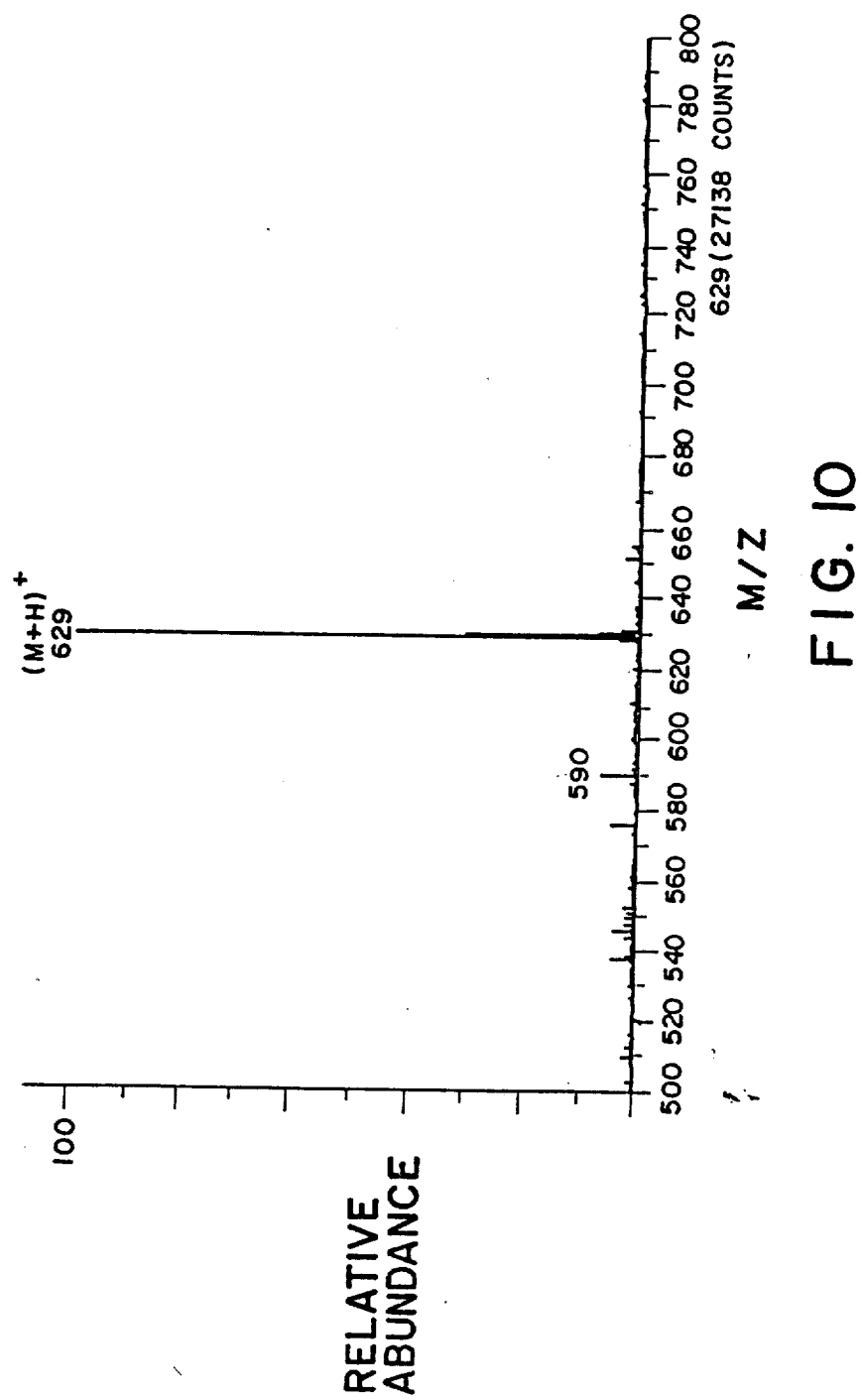
FIG. 10 is a CZE/MS spectrum of peak A from a full scan acquisition of the tryptic digest of recombinant bovine somatotrophin shown in FIG. 8.
Figure 11:
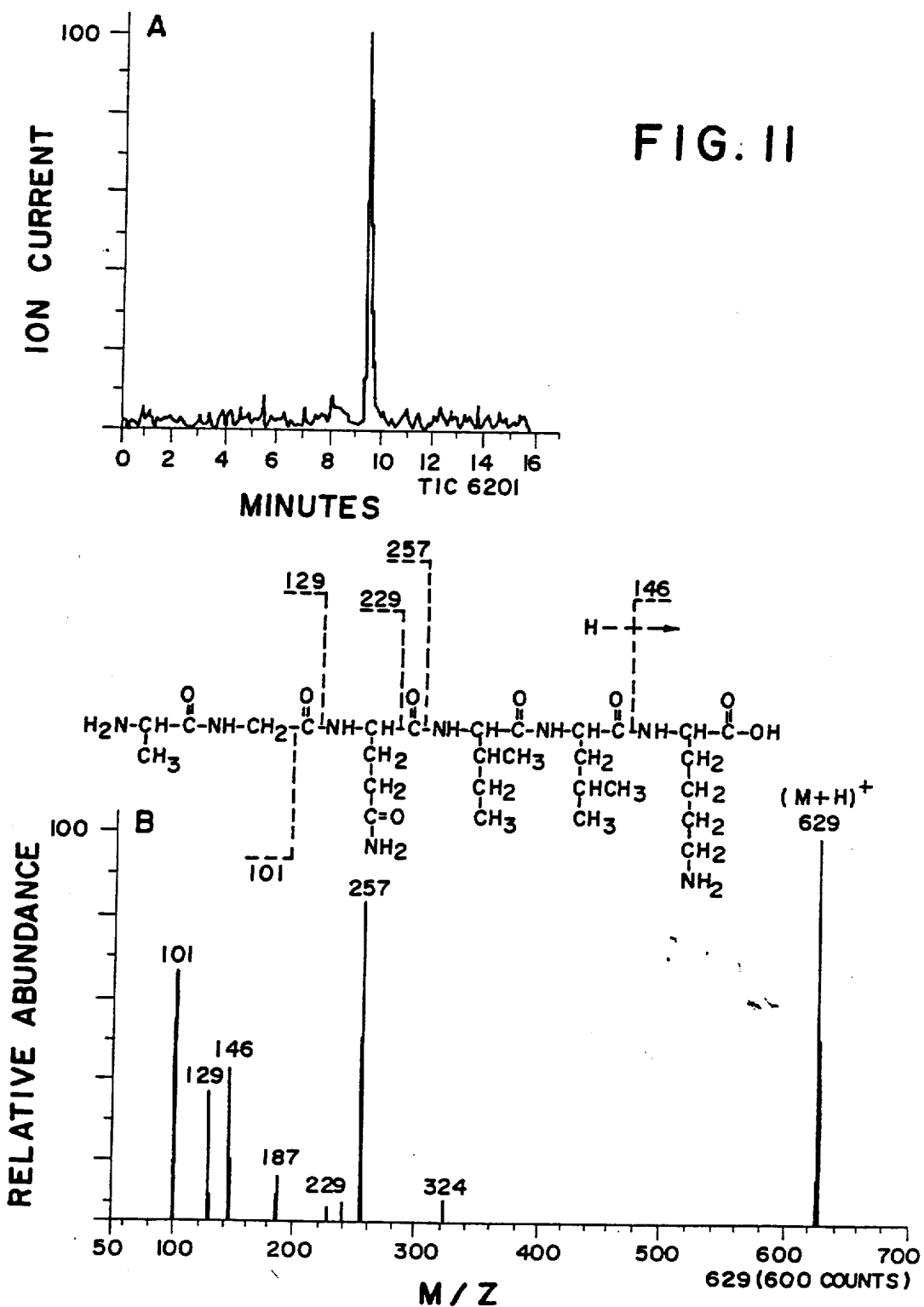
FIG. 11 is a CZE/MS/MS total ion electropherogram (A) and daughter ion mass spectra (B) for peak A FIG. 8 component of tryptic digest.

The full-scan mass spectrum (FIG. 10) of peak A in FIG. 8 is illustrated for a small peptide by ion spray. The mass spectrum of small peptides typically exhibit the $(M+nH)^{n+}$ ion (n=degree of protonation) under the pH conditions used. The degree of protonation is a function of the number of basic functional groups contained within the peptide. Peak A was identified by it's CZE/MS/MS full-scan daughter ion mass spectrum (FIG. 11B). The CZE/MS/MS total ion electropherogram (A) and daughter ion mass spectrum (B) were obtained from injection of the same solution and under the same conditions as the electropherogram shown in FIG. 8. The difference in retention times in FIG. 8 and FIG. 11A can be attributed to the prolonged use of the CZE capillary separation column without conditioning between experiments. As shown (FIG. 11B) the daughter ion mass spectrum is consistent with the sequence of the peptide (AGQILK). These results demonstrated the detection of a peptide in a tryptic digest sample and determining its sequence by CZE/MS/MS.

What is claimed is:

1. A liquid junction interface for coupling a zone electrophoresis separation column with an ion spray chamber/mass spectrometer system wherein said junction comprises a means for adding make-up buffer in an amount which increases the flow rate of the zone electrophoresis column eluent passing to an ion/spray mass spectrometer detector system to make said flow rate compatible with said ion spray/spectrometer in on-line separation/detection of analyte compositions and mixtures; wherein said junction comprises a zone communicating with:
   (1) the exit end of the electrophoresis column;
   (2) a conduit having a first end proximate to (1) but separated therefrom to form a gap and a second end communicating with the ion spray mass spectrometer system;
   (3) a reservoir adapted to contain buffer and to supply said buffer to said zone and to surround (1) and the first end of conduit (2) including the said gap separating (1) and said first end of conduit (2).

2. The apparatus of claim 1 wherein the flow rate of the analyte stream in the electrophoresis separator is from about 0.1 µL to about 1.0 µL per minute and the flow rate of the analyte stream entering the ion spray mass spectrometer is from about 1.0 to about 50 µL/minute.

3. The apparatus of claim 1 wherein said electrophoresis separator is selected from the group consisting of moving boundary electrophoresis, isotachophoresis, zone electrophoresis and isoelectric focusing separators.

4. The apparatus of claim 1 wherein the separator is a capillary zone electrophoresis (CZE) separator.

5. The interface of claim 1 wherein said gap is from about 10 µm to about 25 µm and said eluent flow rate is increased from about 0.1 to 1.0 µL/min to about 1.0 to 50 µL/minute.

6. The interface of claim 5 wherein said gap is from about 20 µm to about 25 µm and the increased flow rate is from about 10 to 20 µL/minute.

7. An apparatus for the analysis of biological fluid analytes which comprises a CZE first capillary column, an on-line mass spectrometer detector for detection and analysis of an analyte having charged particles, an ion spray interface positioned before the mass spectrometer, and further comprising a conduit means adapted to receive the CZE eluent exiting the exit end of the CZE capillary and to deliver it to the said ion spray interface, and a liquid junction interface of claim 6 positioned between the CZE capillary column and the ion spray interface.

8. An apparatus for separating and detecting components of an analyte stream comprising a capillary zone electrophoresis separator (CZE), an ion spray/mass spectrometer (MS) detector system and a means for adding a make-up buffer to the analyte stream between the electrophoresis separator and the ion spray mass spectrometer system in an amount which increases the flow rate of analyte stream exiting the electrophoresis separator and makes it compatible with the flow rate required by the ion spray MS detector and allows detection of the separated components at high sensitivity and without substantial peak broadening; and further comprising a conduit means adapted to receive the CZE eluent exiting the end of the CZE capillary and to deliver the eluent plus make-up buffer to the said ion spray interface; wherein said means for adding make-up buffer comprises the liquid junction of claim 1; the said gap through which make-up buffer passes is from about 10 to 25 µm; said flow rate of the analyte stream is increased from about 0.1 to 1.0 µL/minute to about 1.0 50 µL/minute; the CZE capillary is a fused silica capillary and said conduit is a stainless steel capillary.

9. The liquid junction interface of claim 1, which further comprises a means for adjusting the said gap.

10. The liquid junction interface of claim 1, wherein said ion spray mass spectrometer system is an electrospray/mass spectrometer system.

11. A process for analyzing at high separation efficiencies small amounts of biological samples having one or more analyte components using an electrophoresis column interfaced via a liquid junction with an ion spray chamber/mass spectrometer detector which comprises:
   passing a biological sample through a electrophoresis capillary separation column to separate the analyte components in the eluent stream exiting the electrophoresis column;
   adding make-up buffer to the eluent stream to form an analyte stream consisting of eluent plus make-up buffer;
   detecting at high sensitivity and without peak broadening the said analyte components in an ion spray/mass spectrometer system;
   wherein said make-up buffer is added via the liquid junction in an amount sufficient to increase the flow rate of the analyte stream to make the flow rate compatible with said ion spray/spectrometer in on-line separation/detection of analyte compositions and mixtures; said liquid junction interface comprising a zone communicating with:
   (1) the exit end of the electrophoresis column;
   (2) a capillary conduit having a first end proximate to (1) but separated therefrom to form a gap and a second end communicating with the ion spray/mass spectrometer system;
   (3) a reservoir adapted to contain buffer and to supply said buffer to said zone and to surround (1) and the first end of said conduit (2) including the said gap separating (1) and said first end of conduit (2).

12. The process of claim 11 wherein the CZE column is operated at about 27 kv, the ion spray capillary is at 3 kv, the buffer is 50/50 by volume acetonitrile/30 mM ammonium acetate/acetic acid having a pH of from about 4 to 8.

13. The process of claim 11 wherein the separation efficiency is from about 50,000 to about 1,000,000 theoretical plates.

14. The process of claim 11 wherein the biological sample comprises amino acid sequences, peptide dynorphins, sulfonated azo dyes, leucine enkaphalin, or enzymatic digests.

15. The process of claim 11 wherein the biological sample analyte comprises tryptic digest of recombinant bovine somatotropin.

16. The process of claim 11, wherein said ion spray is an electrospray.

17. The process of claim 11, wherein said junction further comprises a means for adjusting said gap.

18. The process of claim 11, wherein said gap is from about 10 μm to about 25 μm said eluent flow rate is increased from about 0.1 to 1.0 μL/minute to about 1.0 to 50 μL/minute.

19. The process of claim 11, wherein said gap is from about 20 μm to about 25 μm and the increased flow rate is from about 10 to 20 μL/minute.

* * * * *

UNITED STATES PATENT AND TRADEMARK OFFICE
CERTIFICATE OF CORRECTION

PATENT NO. : 4,994,165
DATED : Feb. 19, 1991
INVENTOR(S) : Lee et al

It is certified that error appears in the above-identified patent and that said Letters Patent is hereby corrected as shown below:

Claim 8, column 12, line 27, "1.0 50" should be --1.0 to 50--.

Signed and Sealed this

Twenty-first Day of July, 1992

Attest:

DOUGLAS B. COMER

*Attesting Officer*     *Acting Commissioner of Patents and Trademarks*